US009194858B2

(12) United States Patent
Pezzaniti

(10) Patent No.: US 9,194,858 B2
(45) Date of Patent: Nov. 24, 2015

(54) SYSTEM FOR MEASURING THE CONCENTRATION OF AN ADDITIVE IN A MIXTURE

(75) Inventor: Joseph Larry Pezzaniti, Harvest, AL (US)

(73) Assignee: POLARIS SENSOR TECHNOLOGIES, INC., Huntsville, AL (US)

( * ) Notice: Subject to any disclaimer, the term of this patent is extended or adjusted under 35 U.S.C. 154(b) by 516 days.

(21) Appl. No.: 13/469,995

(22) Filed: May 11, 2012

(65) Prior Publication Data

US 2014/0009751 A1    Jan. 9, 2014

(51) Int. Cl.
| | |
|---|---|
| G01N 33/28 | (2006.01) |
| G01J 3/42 | (2006.01) |
| G01J 3/28 | (2006.01) |
| G01N 21/00 | (2006.01) |
| G01N 21/31 | (2006.01) |
| G01N 21/3577 | (2014.01) |
| G01N 21/17 | (2006.01) |

(52) U.S. Cl.
CPC .............. *G01N 33/2835* (2013.01); *G01J 3/42* (2013.01); *G01N 21/314* (2013.01); *G01N 21/3577* (2013.01); *G01J 3/28* (2013.01); *G01N 21/17* (2013.01)

(58) Field of Classification Search
CPC ....................... G01N 33/2835; G01N 21/3577
USPC ......... 356/301, 319–320, 326–334, 432–437, 356/440–442; 422/82.05, 82.09; 436/164, 436/171
See application file for complete search history.

(56) References Cited

U.S. PATENT DOCUMENTS 4,964,468 A * 10/1990 Adams et al. ................. 166/310
6,300,142 B1 * 10/2001 Andrewes et al. ............ 436/518
(Continued)

FOREIGN PATENT DOCUMENTS

| EP | 2341372 | 7/2011 |
| GB | 2466802 A | 7/2010 |
| WO | 2011/135466 | 3/2011 |

OTHER PUBLICATIONS

International Search Report and Written Opinion mailed Aug. 26, 2013 in corresponding International Application No. PCT/US2013/040490 filed May 10, 2013.

*Primary Examiner* — Gregory J Toatley
*Assistant Examiner* — Hina F Ayub
(74) *Attorney, Agent, or Firm* — Bradley Arant Boult Cummings LLP

(57) ABSTRACT

An apparatus and method for determining a concentration of an additive in a mixture is provided. The apparatus for determining the concentration of an additive in a mixture comprises a distillation system, a filtration system, a detection system and a fluid transportation system. An alternative apparatus is a portable apparatus comprising a distillation system, a filtration system, a detection system and a fluid transportation system removably coupled to a portable container. A method for determining the concentration of the additive in the mixture includes concentrating the additive in the mixture, removing the additive from a fraction of the mixture and measuring a spectral signature of both the non-additive fraction of the mixture and the mixture. A spectral signature value of the non-additive fraction of the mixture to the mixture is determined and then compared to spectral signatures of a plurality of reference mixtures containing known concentrations of the additive.

27 Claims, 7 Drawing Sheets

(56) References Cited

U.S. PATENT DOCUMENTS

| | | | |
|---|---|---|---|
| 6,344,331 B1* | 2/2002 | Ball et al. | 435/7.1 |
| 7,584,791 B2 | 9/2009 | Robb et al. | |
| 2004/0019431 A1* | 1/2004 | Sterling et al. | 702/19 |
| 2004/0082070 A1* | 4/2004 | Jones et al. | 436/8 |
| 2005/0036146 A1* | 2/2005 | Braig et al. | 356/436 |
| 2005/0243321 A1* | 11/2005 | Cohen et al. | 356/432 |
| 2009/0319195 A1 | 12/2009 | Hoots et al. | |
| 2010/0304962 A1* | 12/2010 | Aradi et al. | 502/170 |
| 2011/0196179 A1 | 8/2011 | Bradin | |
| 2013/0215426 A1* | 8/2013 | Kaushal et al. | 356/436 |
| 2014/0228710 A1* | 8/2014 | Butler et al. | 600/581 |

* cited by examiner

SYSTEM FOR MEASURING THE CONCENTRATION OF AN ADDITIVE IN A MIXTURE

FIELD OF THE INVENTION

The present invention is directed to an apparatus and method for analyzing a mixture containing an additive, and more particularly, to a system for calculating the concentration of a fuel additive in a fuel using a differential spectroscopic analysis combined with a filtration step.

BACKGROUND OF THE INVENTION

Use of spectrometry for analysis of liquid mixtures, such as fuel, is known in the art. For example, U.S. Pat. No. 5,262,645 describes a method for measuring alcohol concentration in an alcohol/gasoline mixture by passing light through the mixture at a first wavelength that is strongly absorbed by the alcohol and weakly absorbed by the gasoline and at a second wavelength that is weakly absorbed by the alcohol and strongly absorbed by the gasoline. An absorbance ratio based upon absorbance measurements taken of the mixture at both wavelengths is computed. From this ratio and fuel temperature the concentration of alcohol in the fuel is determined.

There are two major difficulties associated with measuring additive concentrations in fuels using infrared (IR) spectroscopy. A fuel additive's spectral signature at its characteristic transmission peak can be extremely small. As a result, concentration of a fuel additive in a mixture can be at or below the detection threshold. Also, the background spectral variation of the fuel mixture is typically large compared to the spectral signature of the fuel additive, leading to interference in the spectral signature of the fuel additive.

SUMMARY

The present invention is directed to a method and apparatus for determining the concentration of an additive in a mixture. More particularly, the present invention is directed to a method and apparatus for determining the concentration of a fuel additive, such as a corrosion inhibitor, a static dissipater, an icing inhibitor, a thermal stability improver, an antioxidant, a metal deactivator, and/or an ignition improver, in a fuel mixture such as gasoline, diesel fuel and jet fuel.

According to one aspect of the invention, there is provided a method for calculating the concentration of an additive in a mixture, the method including removing the additive from a portion of the mixture to create a first sample of the mixture with an approximate concentration of zero for the additive. A plurality of reference mixtures is then selected with each reference mixture containing a known quantity of the additive. Each reference mixture is separated into a pair of reference samples with each pair of reference samples including a first reference sample and a second reference sample. Thereafter, the additive is removed from each of the first reference samples, and the absorption spectrum of the first sample, the mixture, each of the first reference samples and each of the second reference samples is measured. An absorption spectrum ratio for the first sample and the mixture is computed, as well as an absorption spectrum ratio for the first reference sample and the second reference sample for each pair of reference samples. The absorption spectrum ratio for the first sample and the mixture is compared to the absorption spectrum ratio for each pair of reference samples to calculate the concentration of additive in the mixture. Optionally, the concentration of the additive in the mixture can be increased prior to creating the first sample. This may be required if the concentration of the additive in the mixture is substantially small thereby requiring detection capabilities at lower concentration thresholds.

When analysis of the mixture in the field is desired, the steps of increasing the additive concentration, removing the additive from the mixture and measuring an absorption spectrum of the first sample and the mixture are carried out using an instrument that integrates an additive concentration device, an additive removal device, a transmission spectrometer and a fluid transport system. For portability purposes, such an instrument can be coupled to and housed within a readily portable, carrying case weighing under fifteen pounds.

According to another aspect of the invention, there is provided a method for calculating an additive concentration in a mixture, the method including directing a first sample of the mixture through a fluid transportation system to an additive removal device that removes the additive from the first sample, followed by directing the first sample from the additive removal device and through the fluid transportation system to a first beam of light transmitted by a transmission spectrometer. A second sample of the mixture is directed through the fluid transportation system to a second beam of light transmitted by the transmission spectrometer. The transmission spectra information for the first sample and the second sample is measured, followed by calculating a ratio based upon the transmission spectra information for the first sample and the second sample. The concentration of the additive in the mixture is then computed by comparing the ratio based upon the transmission spectra information for the first sample and the second sample to transmission spectra information of other mixtures containing known quantities of the additive. Optionally, the additive in the mixture is concentrated prior to removing the additive from the first sample and prior to directing the second sample through the fluid transportation system to the second beam of light.

According to yet another aspect of the invention, there is provided a method of calculating an additive concentration in a mixture, the method including measuring a first transmission spectrum of a first sample of the mixture, wherein the first sample excludes an additive, measuring a second transmission spectrum of a second sample of the mixture, wherein the second sample includes the additive, and calculating a spectrum transmission ratio based upon the first transmission spectrum and the second transmission spectrum. Thereafter, the spectrum transmission ratio is compared to a plurality of transmission spectrum ratios obtained from other mixtures containing known quantities of the additive.

The mixtures containing known quantities of the additive can be prepared in any number of ways know in the art. In many instances, these mixtures are prepared by obtaining a fraction of the mixture, removing essentially all of the additive from the fraction to form an additive-free mixture, separating the additive-free mixture into a plurality of samples, and adding varying, predetermined amounts of the additive to the plurality of samples.

DETAILED DESCRIPTION

The present apparatus and method are used to determine the concentration of an additive in a mixture. The components of the apparatus act in concert to first concentrate the additive in the mixture, then remove the additive from a fraction of the mixture thereby creating a first sample without additive and a second sample with additive. Transmission spectra are then determined for the first and the second samples, which are used to compute a transmission spectra ratio. The transmission spectra ratio is then compared to transmission spectra of a plurality of reference mixtures with known amounts of additive in the reference mixtures to determine the concentration of the additive in the original mixture.

Figure 1:
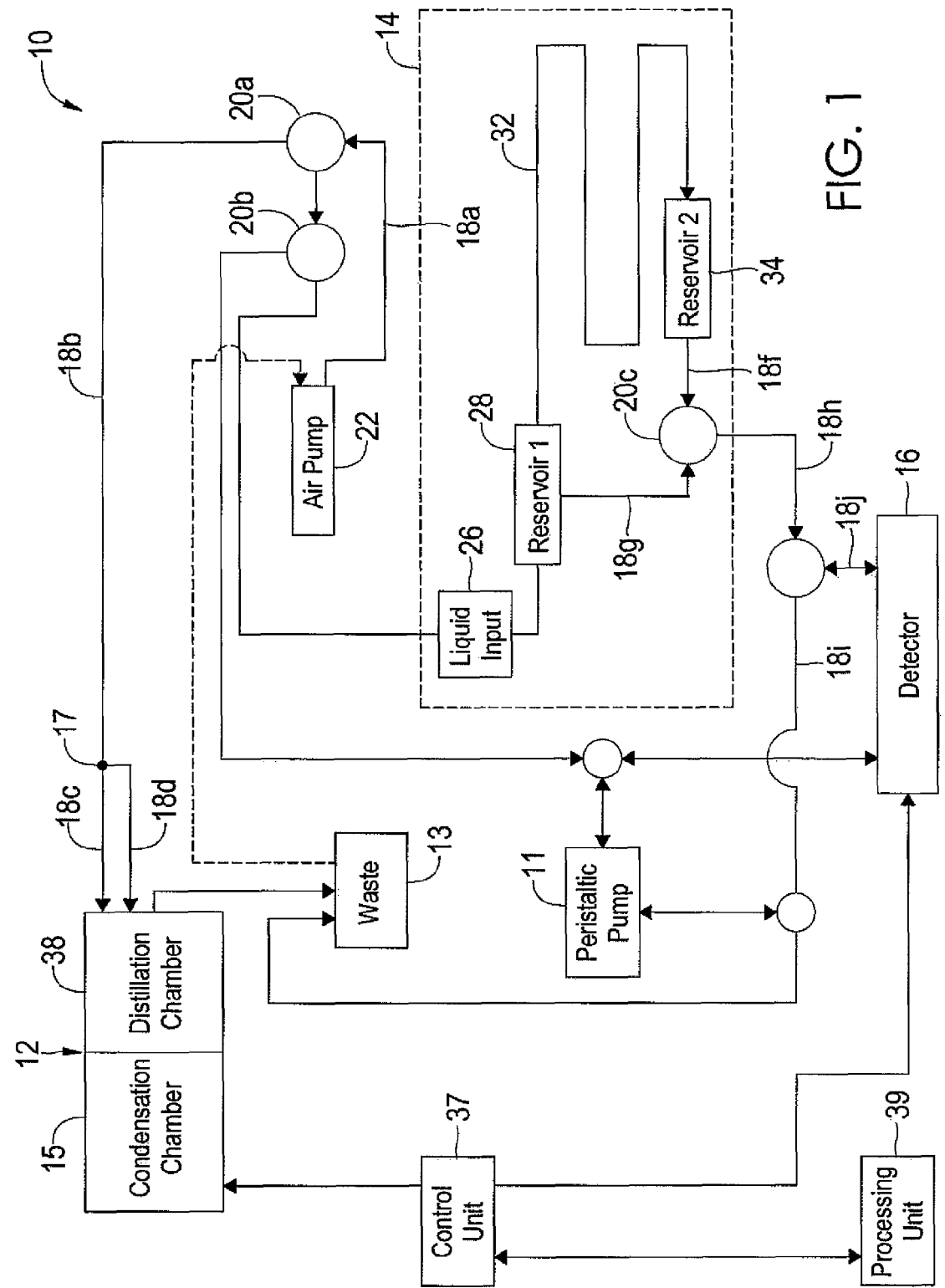
FIG. 1 is a schematic view of a system for measuring the concentration of an additive in a mixture.

FIG. 1 depicts an overview of an apparatus 10 used to measure the concentration of an additive in a mixture. Apparatus 10 includes a distillation system 12, a filtration system 14, a detector system 16, and a fluid transportation system for coupling systems 12, 14 and 16 to one another, all of the systems being in communication with a control unit 37 and an associated processing unit 39. Control unit 37 and processing unit 39 allow a user to control and monitor the temperature of distillation system 12, the flow rate of fluid through the fluid transportation system, the flow rate of air and all operations of apparatus 10. The system further includes an air pump 22, a peristaltic pump 11, a waste receptacle 13, an input for filtration system 14 and a pair of reservoirs 28 and 34.

When the apparatus is in use, a mixture containing an additive is distilled after being injected into distillation system 12. The concentrated mixture containing the additive is sent to an input 26 of the filtration system 14, where it then enters a first reservoir 28. Sample 1, a first fraction of the concentrated mixture, is sent from first reservoir 28 through filter 32 where the additive of sample 1 is removed by an additive-removing substrate located in the interior of filter 32. After sample 1 is filtered, it is sent through a second reservoir 34 to detector system 16 where detector 83 measures the transmission spectra for sample 1. Sample 1 is then sent to waste receptacle 13. Once sample 1 is moved out of detector system 16, sample 2, a second fraction of the concentrated mixture, is sent from first reservoir 28 to second reservoir 34, bypassing filter 32 and retaining the additive in sample 2. Sample 2 is then sent to detector system 16 and detector 83 measures the transmission spectra for sample 2. The transmission spectra of both sample 1 and sample 2 is transmitted from detector 83 to processing unit 39 which then calculates the transmission spectra ratio for sample 1 to sample 2. This transmission spectra ratio of sample 1 to sample 2 correlates to the concentration of the additive in the original mixture.

Figure 2:
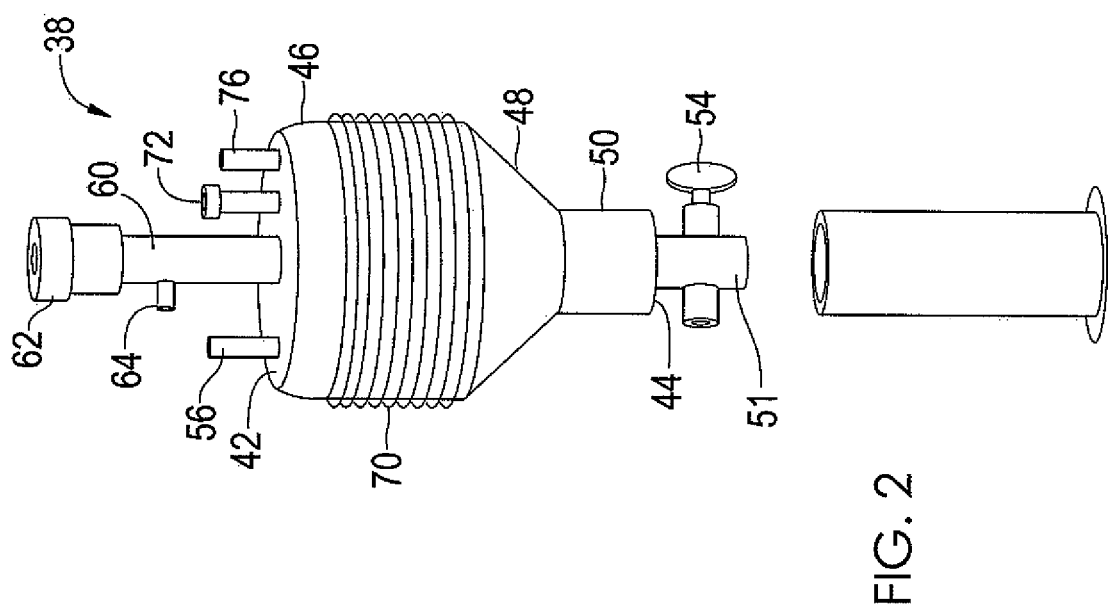
FIG. 2 is a perspective view of a distillation apparatus for use in the system of FIG. 1.

Use of distillation system 12 is required if the concentration of the additive in the mixture is at or below the detection threshold of detector system 16 or is so low as to be masked by background interference from the mixture. More particularly referring to FIGS. 1 and 2, distillation system 12 includes a condensation chamber 15 in communication with a distillation chamber 38. Distillation chamber 38 consists of three contiguous chambers: an upper chamber 46, a conic transition chamber 48 and a lower chamber 50. Upper chamber 46 and lower chamber 50 are cylindrical with upper chamber 46 having a larger diameter than lower chamber 50. Conic transition chamber 48 connects upper 46 to lower chamber 50. Opening 44 of lower chamber 50 is contiguous with an outlet, the outlet being coupled to a stopcock 54. Stopcock 54 allows a user to start and/or stop liquid exiting lower chamber 50.

For air flow into and out of distillation chamber 38, air pump 22 moves air from a first tube 18a through a first switch valve 20a and a second tube 18b where second tube 18b is removably coupled to via a splitter 17. Splitter 17 allows the air flow to be split from second tube 18b into two tubes, a third tube 18c and a fourth tube 18d, each removably coupled to distillation chamber 38. More particularly referring to FIGS. 1 and 3, third tube 18c is removably coupled to a first opening 56 located on a top side 42 of distillation chamber 38 allowing air flow into distillation chamber 38. Fourth tube 18d is removably coupled an air bubbler that extends into the interior of distillation chamber 38 through a second opening 76. A side port 64 located on a lateral side of a third opening 60 of top side 42 is removably coupled to condensation chamber 15, providing an outlet for vapor to be moved from distillation chamber 38 to condensation chamber 15 via a tube 66.

Figure 3:
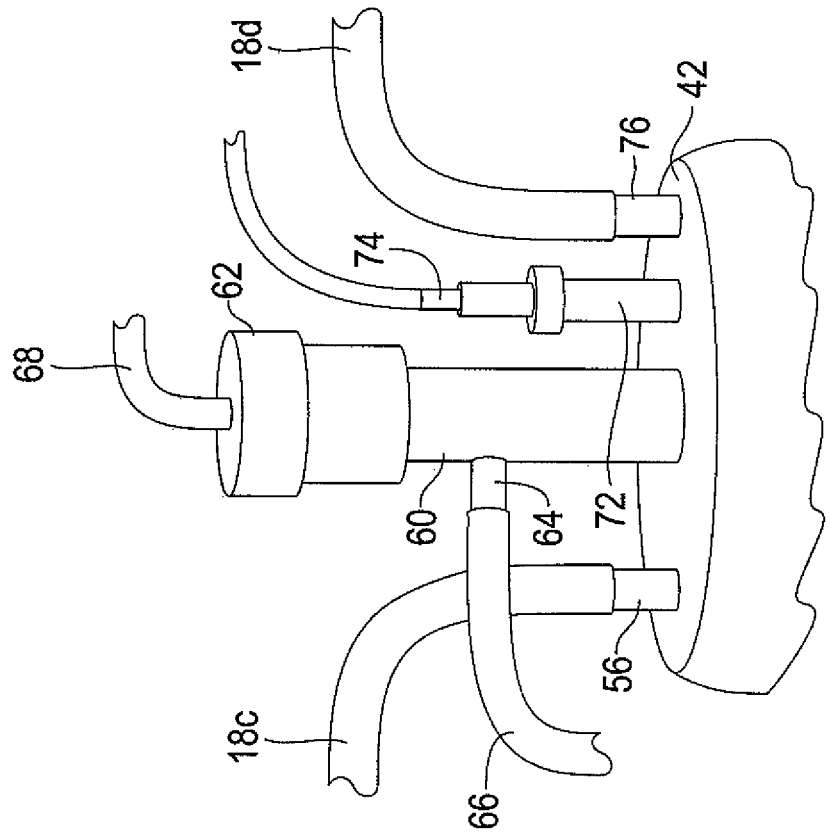
FIG. 3 is a partial, perspective view of a top of the distillation apparatus of FIG. 2.

Referring to FIG. 3, third inlet 60 on top side 42 of distillation chamber 38 houses a detachable cartridge heater 62. Detachable cartridge heater 62, connected to a power source via a power cord 68, raises the temperature of upper chamber 46 to a desired temperature range for distillation. The desired temperature range is chosen to be high enough to vaporize higher vapor pressure liquids but low enough to be below the vaporization temperature of the additive. To monitor the temperature of cartridge heater 62 either manually or via processing unit 39, a first thermocouple is coupled with cartridge heater 62.

Alternatively, cartridge heater 62 can be replaced by a plurality of heating coils 70 or other materials capable of raising the temperature of upper chamber 46. For example, heating coils 70 can be removably affixed about the outer circumference of upper chamber 46. In this embodiment, the first thermocouple is coupled to heating coils 70 to monitor temperature of heating coils 70.

Third opening 60 on top side 42 of distillation chamber 38 also functions as a sample inlet. A syringe or other conventional method is temporarily coupled to third opening 60 to inject the mixture containing the additive into distillation chamber 38.

A second thermocouple 74 is removably coupled to a fourth opening 72 of top side 42 of distillation chamber 38. A user can monitor the temperature of the mixture containing the additive in upper chamber 46 of distillation chamber 38 via second thermocouple 74 and maintain the temperature of the mixture containing the additive within the desired temperature range. Processing unit communicates with cartridge heater 62 or alternate heating method in such a way as to be able to adjust the temperature of cartridge heater 62 or alternate heating method to remain in the desired temperature range.

Figure 4:
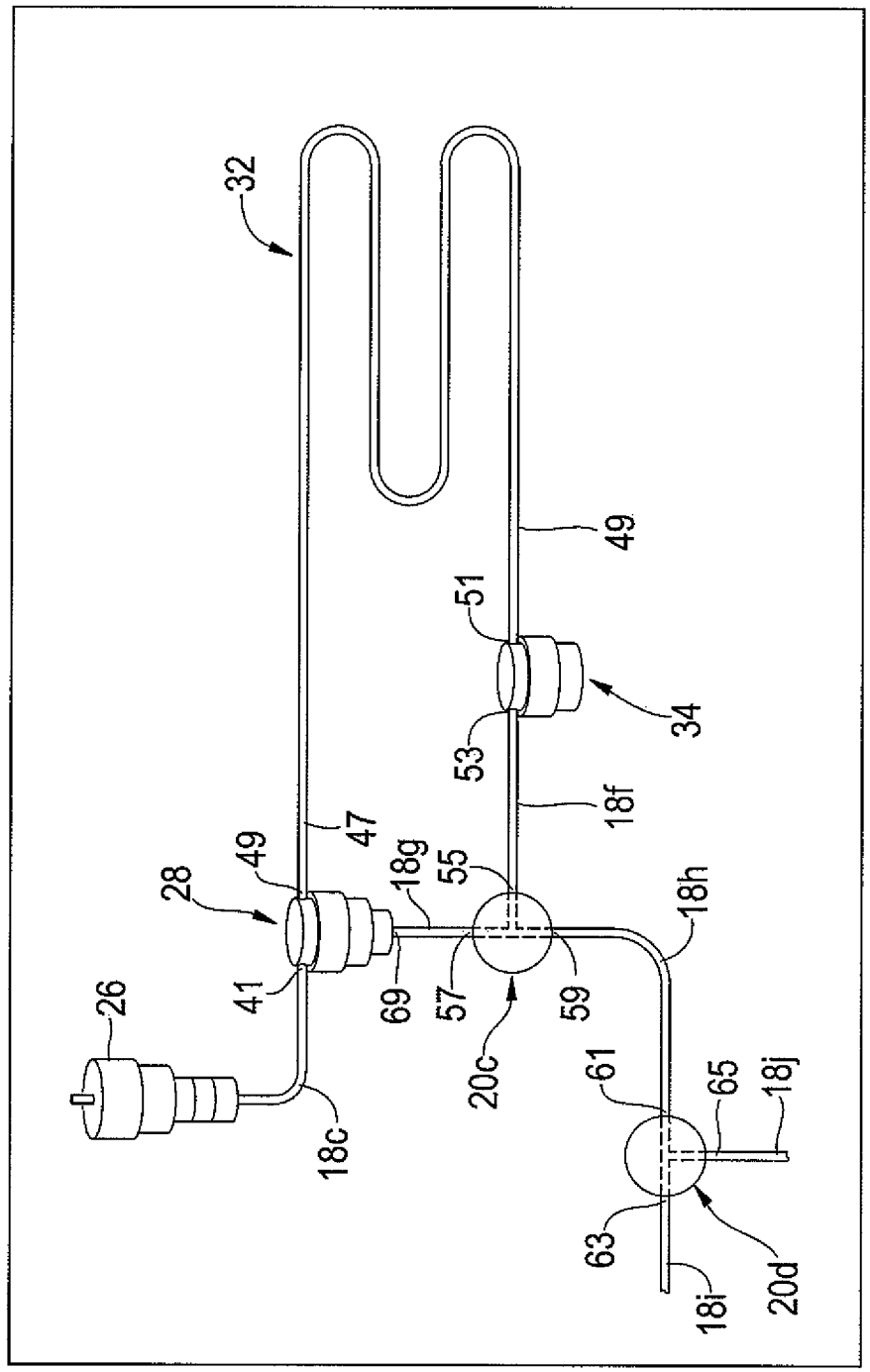
FIG. 4 is a perspective view of a filtration apparatus for use in the system of FIG. 1.

Referring to FIGS. 1 and 4, distillation system 12 communicates with input 26 of filtration system 14. Input 26 is removably coupled to first reservoir 28 at an inlet 41 by a fifth tube 18e. An outlet 49 of first reservoir 28 is removably coupled to a first end 47 of filter 32. Filter 32 is composed of a tube filled with a substrate chosen to target and remove an additive in a mixture. As those familiar in the art understand, complete removal of the additive from the mixture by filtration requires both a substrate that attracts and separates, thereby retaining, the additive, allowing an additive-free mixture to exit the filtering mechanism and sufficient time for the additive in the mixture to be exposed to the substrate. Time of exposure to the substrate is controlled by flow rate of the mixture containing the additive and the length of the filter 32. A second end 49 of filter 32 is coupled to an inlet 51 of second reservoir 34. An outlet 53 of second reservoir 34 is coupled to a first inlet 55 of third switch valve 20c by a sixth tube 18f.

A second outlet 69 of first reservoir 28 is removably coupled to a second inlet 57 of third switch valve 20c by a seventh tube 18g. An outlet 59 of third switch valve 20c is coupled to an inlet 61 of fourth switch valve 20d via an eighth tube 18h.

A first opening 65 of fourth switch valve 20d is coupled to waste receptacle 13 via a ninth tube 18i. Peristaltic pump 11 facilitates the movement of a waste product from detector system 16 through fourth switch valve 20d and then to waste receptacle 13.

Figure 5:
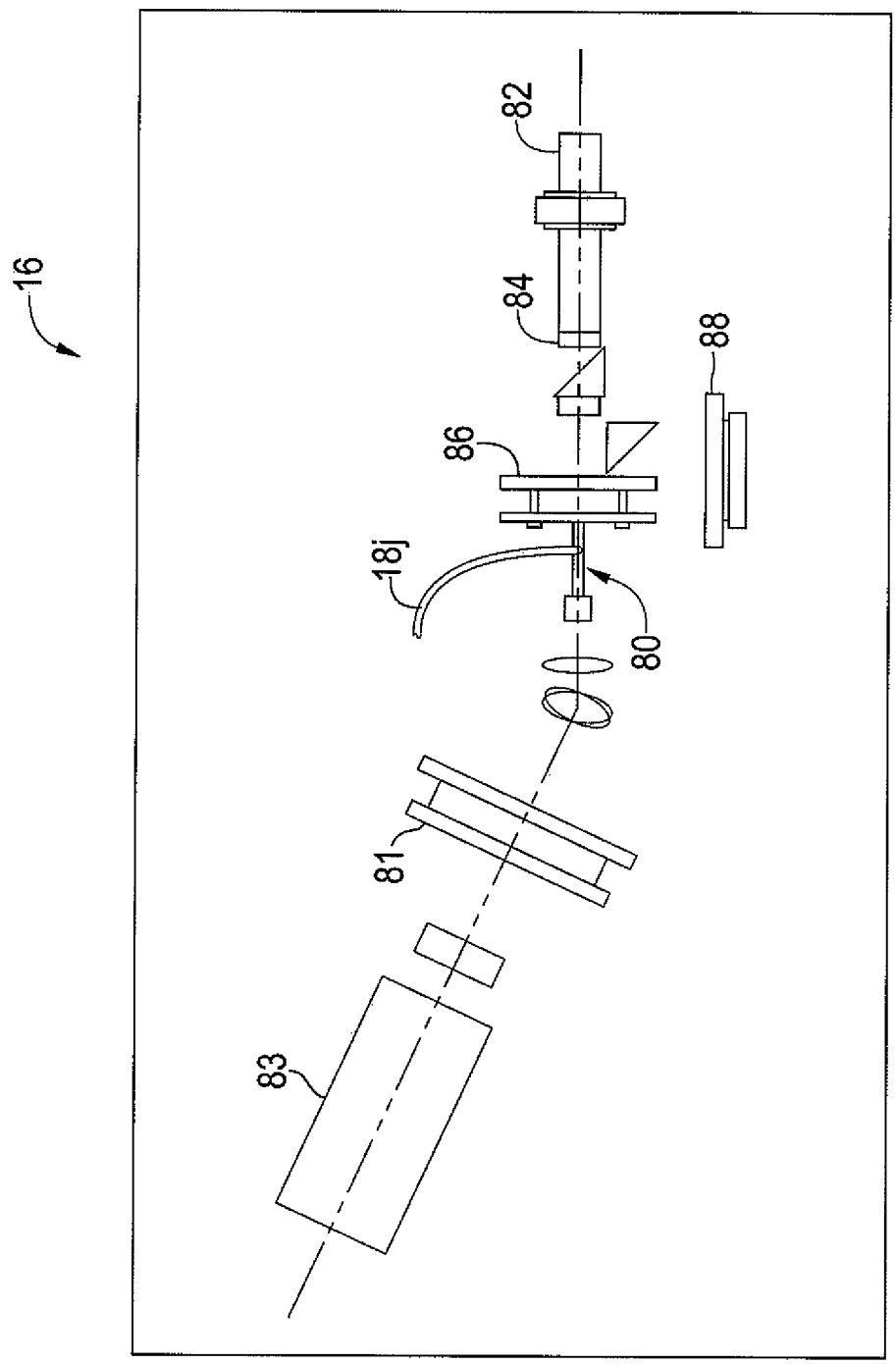
FIG. 5 is a top plan view of a detection apparatus for use in the system of FIG. 1.

Referring to FIGS. 4 and 5, filtration system 14 is coupled to detector system 16 between a second opening 65 of fourth switch valve 20d and a cuvette 80 of detector system 16 via a tenth tube 18J. Referring more particularly to FIG. 5, detector system 16 comprises a light source 82, a lens 84, a moveable reference mirror 86, a constant temperature cold plate 88, cuvette 80, a multi-position filter wheel 81 and a detector 83. Detector system 16 measures a transmission or absorbance spectra for a sample by passing a first light beam from light source 82 through lens 84 and then through the sample in cuvette 80. The first light beam is then focused onto multi-position filter wheel 81 and sent to detector 83 where detector 83 determines the transmission or absorption spectra of the sample.

To correct the transmission or absorption spectra of the sample for any background interference, detector system 16 adjusts reference mirror 86 so that reference mirror 86 reflects a second light beam to constant temperature cold plate 88. Constant temperature cold plate 88 sends the second light beam to multi-position filter wheel 81 and detector 83, where detector 83 measures a transmission or absorption spectra for the background where the second light beam carries no information of the sample. To determine a corrected transmission or absorption spectra for the sample, the transmission or absorption spectra for the sample is mathematically corrected with the transmission or absorption spectra for the background by any conventional method.

Figure 6:
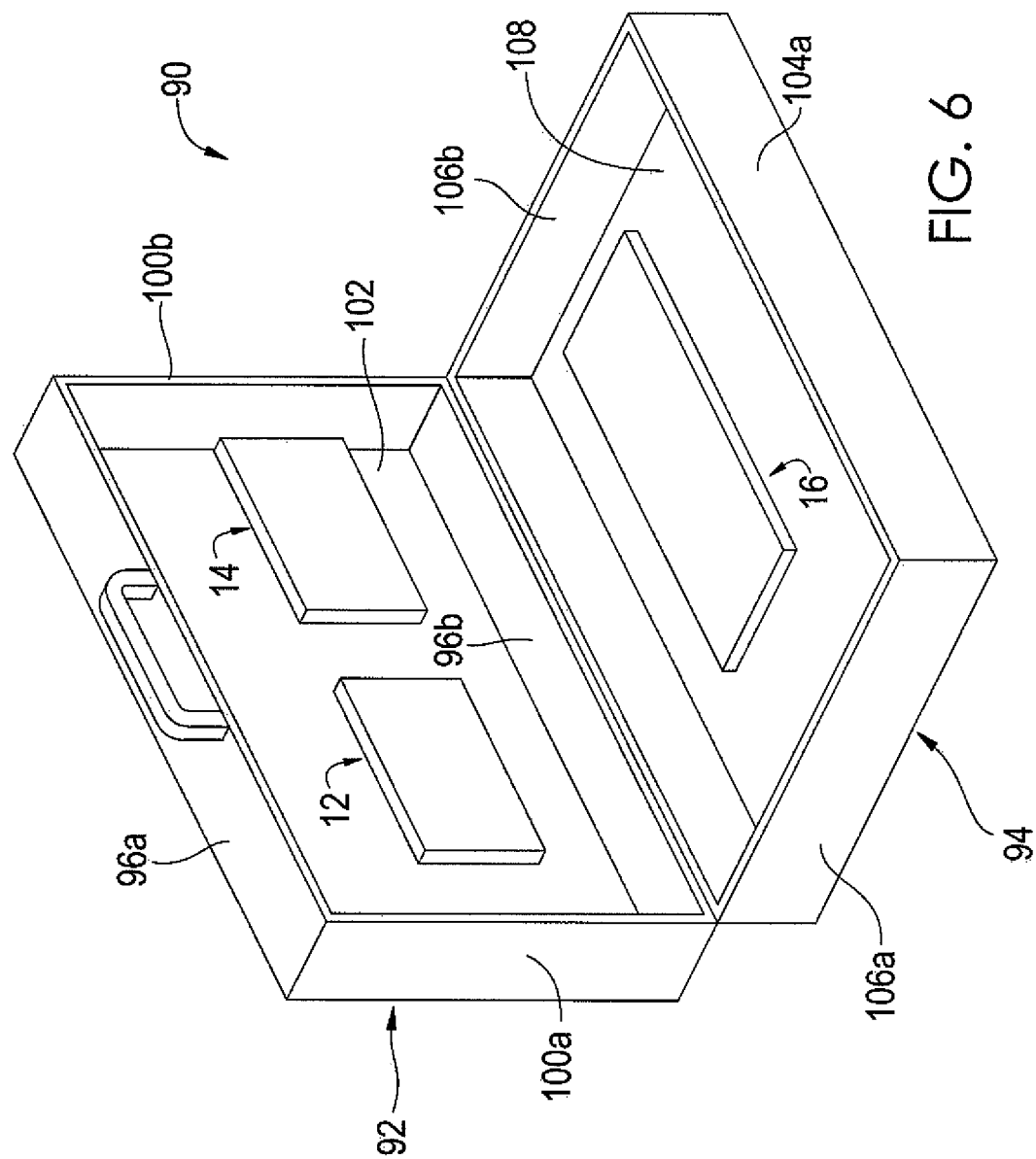
FIG. 6 is a perspective view of a portable case for containing the system of FIG. 1.

Referring to FIG. 6, a portable container 90 contains distillation system 12, filtration system 14, detection system 16 and all or part of the fluid transportation system. Portable container 90, in a closed state, forms a hollow, approximately square or rectangular-shaped body. Portable container 90 is composed of a first hard shell 92 and a second hard shell 94. First hard shell 92 has two end walls 96a and b, two side walls 100a and b and a back wall 102. Second hard shell 94 has two end walls 104a and b, two side walls 106a and b and a back wall 108. First 92 and second hard shell 94 are coupled in any conventional manner as to allow first 92 and second hard shell 94 to meet where end walls 98a and b of first hard shell 92 align with end walls 104a and b of second hard shell 94 and side walls 100a and b of first hard shell 92 align with side walls 106a and b of second hard shell 94 when portable container 90 is in the closed state. First 92 and second hard shell 94 can be composed of rigid plastic or any other conventional materials available. Portable container 90 can be secured in its closed position by at least one latch using any conventional manner in which to secure a container.

Within the open space of the interior of portable container 90, the distillation system 12, filtration system 14 and detector system 16 can be removably coupled to portable container 90. Distillation system 12, filtration system 14 and detector system 16 can be removably coupled to interior side of back wall 102 of first hard shell 92 either directly with any conventional means or indirectly by removably coupling each system 12, 14 and 16 to a body of material, such as a board, that is able to be placed inside portable container 90. The body of material can then be removably coupled to the interior space of portable container 90 by epoxy, screws or other conventional means. The body of material can be composed of a at least one of a plurality of materials, including wood, plastic, acrylic or any conventional materials available now.

Distillation system 12 is removably coupled to the interior side of back wall 102 of first hard shell 92 where top side 42 of distillation chamber 38 is oriented toward end wall 98a of first hard shell 92 and condensation chamber 15 is adjacent to side wall 100a. Filtration system 14 is removably coupled to the interior side of back wall 102 of first hard shell 92 whereby filtration system 14 is adjacent to distillation system 12. Input 26 of filtration system 14 is adjacent to end wall 98a of first hard shell 92 and filter 32 is adjacent to side wall 100b. Detector system 16 is removably coupled to interior back wall 108 of second hard shell 94.

Figure 7:
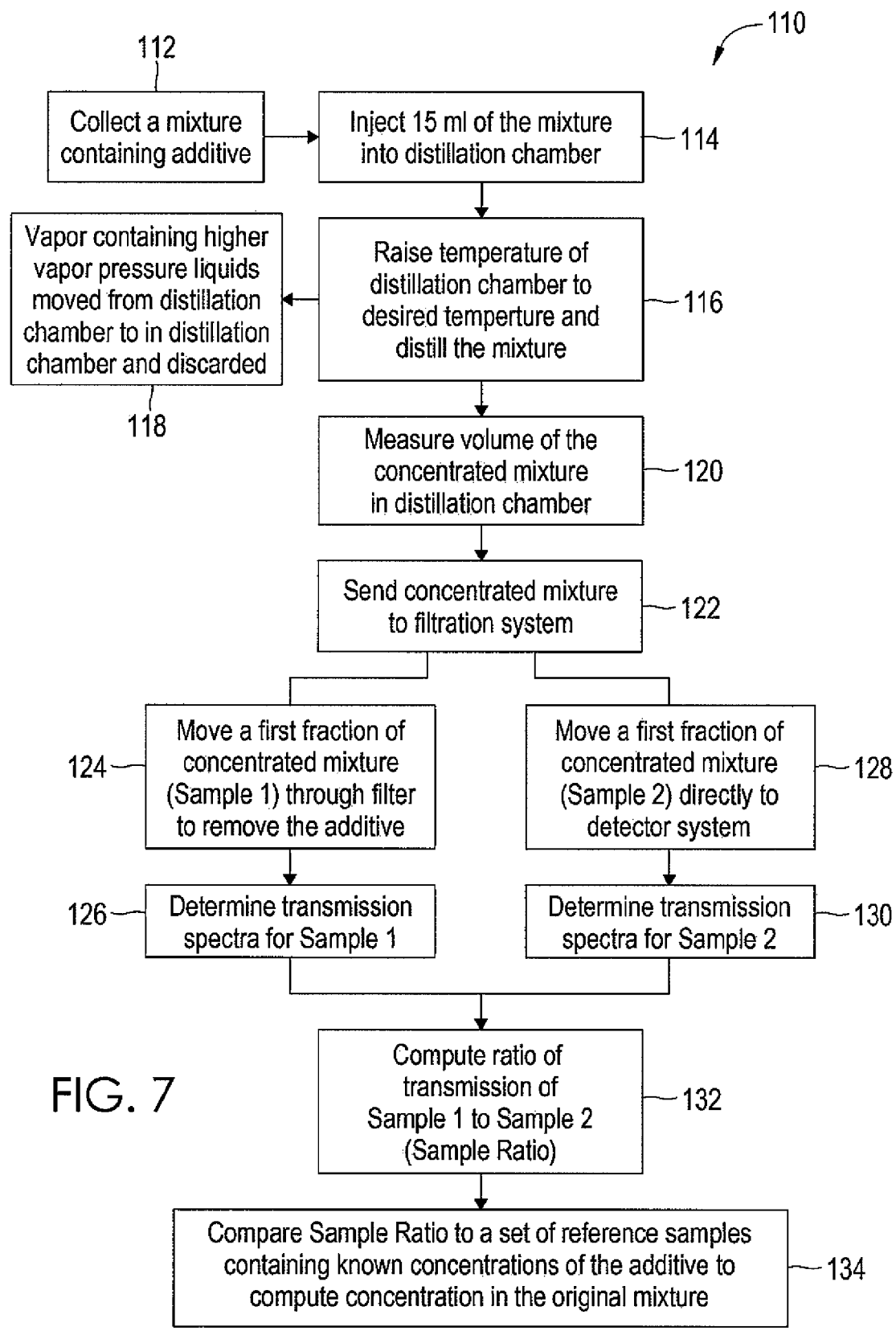
FIG. 7 is a flowchart depicting a method for determining the concentration of an additive in a mixture.

As illustrated in FIG. 7, a method for measuring a concentration of an additive in a mixture is executed as described below.

The mixture containing the additive is collected 112 and placed 114 in distillation chamber 38 by injecting the mixture containing the additive through third opening 60 on top side 42. Cartridge heater 62 is removably coupled to third opening 60 then turned on and set at a level to bring the temperature of upper chamber 46 into a desired temperature range that vaporizes higher vapor pressure liquids but is low enough to not vaporize the additive 116. Second thermocouple 74 is removably placed into fourth opening 72 of top side 42. Second thermocouple 74 is turned on and set up to communicate with processing unit 39, allowing a user to monitor the temperature in distillation chamber 38. The first thermocouple removably coupled to cartridge heater 62 is turned on and set up to communicate with processing unit 39, allowing the user to monitor the temperature of the cartridge heater 62.

Air pump 22 is turned on, providing air flow into distillation chamber 38 and apparatus 10. Air flow is pumped from air pump 22 into first opening 56 of top side 42 to the interior of distillation chamber 38, thus facilitating temperature stabilization of distillation chamber 38 as well as forcing vapor containing vaporized higher vapor pressure liquids out of distillation chamber 38 and into condensation chamber 40, 118. Air flow from air pump 22 is moved to fourth tube 18d removably coupled to an air bubbler that extends through second opening 76 and into the interior of distillation chamber 38. The air flow flowing through the air bubbler agitates the mixture containing the additive in distillation chamber 38 during the time required to reach the desired concentration of the additive for distillation. The mixture containing the additive is distilled 116 for the period of time required to reach the desired concentration of the additive in the mixture.

At the conclusion of the time required to reach the desired concentration of the additive in the mixture 116, cartridge heater 62 is turned off and the concentrated mixture containing the additive in distillation chamber 38 is allowed to cool. The stopcock 54 of distillation chamber 38 is opened and the concentrated mixture containing the additive is moved from distillation chamber 38 through open end 50. The volume of the concentrated mixture containing the additive is determined 120.

As stated above, air flow is started through apparatus 10 by air pump 22 prior to distillation or introducing a sample into filtration system 14. The air flow moves 122 the concentrated mixture into input 26 of filtration system 14 from distillation system 12. The concentrated mixture containing the additive in input 26 is then sent to first reservoir 28. Sample 1, a fraction of the concentrated mixture containing the additive, is moved 124 from first reservoir 28 to filter 32. Filter 32 removes the additive from sample 1 of the concentrated fuel mixture as it moves from first end 47 of filter 32, through filter 32 and exiting second end 49 of filter 32. Sample 1 is then sent to second reservoir 34.

From second reservoir 34, sample 1 is sent to detector system 16 via third switch valve 20c and fourth switch valve 20d. Upon moving into detector system 16, sample 1 is deposited into cuvette 80 of detector system 16. A transmission spectra for sample 1 is made with reference mirror 86 in a position to allow a first light beam from a light source 82 to pass through cuvette 80 and sample 1. The first light beam is then focused on multi-position wheel 81 and sent to detector 83 where detector 83 measures the first transmission spectra for sample 1. A transmission spectra is determined for the background with reference mirror 86 in a position to cause a second light beam to hit reference mirror 86, but not cuvette 80. Reference mirror 86 reflects the second light beam to constant temperature cold plate 88. The second light beam then is focused on multi-position filter wheel 81 and sent to detector 83 where detector 83 measures the transmission spectra for the background. The transmission spectra for sample 1 and the transmission spectra for the background are sent to processing unit 39 where processing unit 39 determines a transmission spectra for sample 1 correcting for the background 126.

After the transmission spectra is determined for sample 1, sample 1 is sent from cuvette 80 to fourth switch valve 20d and then deposited in waste receptacle 13. Sample 2, the remaining fraction of the concentrated fuel mixture in first reservoir 28, is moved from first reservoir 28 to third switch valve 20c. From third switch valve 20c, sample 2 is sent to fourth switch valve 20d and then to cuvette 80 of detector system 16, thereby bypassing filter 32 leaving the additive intact in sample 2, 128.

With sample 2 in cuvette 80, a transmission spectra for sample 2 is made with reference mirror 86 in a position to allow a first light beam from a light source 82 to pass through cuvette 80 and sample 2, 130. The first light beam is then focused on multi-position wheel 81 and sent to detector 83 where detector 83 measures the transmission spectra for sample 2. A transmission spectra is determined for the background with reference mirror 86 in a position to cause a second light beam to hit reference mirror 86, but not cuvette 80. Reference mirror 86 reflects the second light beam to constant temperature cold plate 88. The second light beam then is focused on multi-position filter wheel 81 and sent to detector 83 where detector 83 measures the transmission spectra for the background. The transmission spectra for sample 2 and the transmission spectra for the background are sent to processing unit 39 where processing unit 39 determines a transmission spectra for sample 2 correcting for the background. Sample 2 is then sent from cuvette 80 to fourth switch valve 20d and then to waste receptacle 13.

A transmission spectra ratio for sample 1 to sample 2 is then determined 132. A plurality of transmission spectra ratios for a plurality of reference mixtures with each reference mixture containing a known concentration of the additive are determined as with the above method. To calculate the concentration of the additive in the mixture, the transmission spectra ratio for sample 1 to sample 2 is mathematically compared to the plurality of transmission spectra ratios for the plurality of reference mixtures using a means such as partial least squares regression 134.

A mathematical relationship between the transmission spectra of sample 1 and sample 2 can be determined 132 in ways other than a ratio, including, but not limited to, subtraction, weighted subtraction, mathematical modeling, parametric or nonparametric statistical analysis or with the use of any other mathematical or statistical tool. Additionally, the mathematical or statistical relationship between the plurality of transmission spectra for the plurality of reference mixtures with each reference mixture containing a known concentration of the additive can be determined in other ways, including, but not limited to, subtraction, weighted subtraction, mathematical modeling, parametric or nonparametric statistical analysis or with the use of any other mathematical or statistical tool. To compute the concentration of the additive in the mixture, the mathematical or statistical tool chosen to compute the mathematical relationship between the transmission spectra value for sample 1 and sample 2 must be used for calculation of the mathematical relationships for the plurality of transmission spectra for the plurality of reference mixtures. To calculate the concentration of the additive in the mixture, the transmission spectra relationship between sample 1 to sample 2 is then compared to the plurality of transmission spectra relationships for the plurality of reference mixtures using a mathematical or statistical means 134 (e.g. partial least squares regression).

The following Example is for illustrative purposes only and does not necessarily limit this invention.

EXAMPLE

The concentration of a corrosion inhibitor additive in a fuel mixture was determined for a plurality of fuel mixtures collected from at least one fuel distribution point. Cartridge heater 62 from third opening 60 of distillation chamber 38 was removed to place a fuel mixture containing the corrosion inhibitor additive in distillation chamber 38. Using a syringe, 15 ml of the fuel mixture was injected into distillation chamber 38 aiming the syringe straight down so that the fuel mixture did not hit a sidewall of distillation chamber 38. After injection, cartridge heater 62 was reinserted to third opening 60 of distillation chamber 38. Once cartridge heater 62 was fully seated, creating a seal, care was taken so cartridge heater 62 was not in direct contact with second thermocouple 74.

Air pump 22 was turned on to allow air flow to distillation chamber 38. Second thermocouple 74 was placed into fourth opening 72 of top side 42 of distillation chamber. Second thermocouple 74 was turned on and set up to communicate with processing unit 39. The first thermocouple removably coupled to cartridge heater 62 was turned on and set up to communicate with processing unit 39. A first air flow controller associated with distillation system 12 was oriented to send air flow to an air bubbler removably coupled to second opening 76 of distillation chamber 38 so the air flow from the air bubbler mixed the fuel mixture during distillation. Airflow is sufficient for mixing if the bubble path is random, but does not continuously splash the fuel mixture onto interior top side 42 of distillation chamber 38. A second airflow controller associated with distillation system 12 was oriented to send air flow into first opening 56 of distillation chamber 38 providing air movement in distillation chamber 38, facilitating the movement of vaporized higher vapor pressure liquids out of distillation chamber 38 and into condensation chamber 40 while assisting in the stabilization of the temperature of distillation chamber 38.

After air flow from air pump 22 began flowing into distillation chamber 38, cartridge heater 62 was turned on. The first thermocouple removably coupled to cartridge heater 62 provided continuous measurements of cartridge heater's 62 temperature which was recorded and monitored by processing unit 39. Processing unit 39 adjusted cartridge heater 62 to maintain a desired temperature range in distillation chamber 38.

Second thermocouple 74 provided continuous measurements of the interior temperature of upper chamber 46 of distillation chamber 38 which was monitored and maintained between 180° C. and 190° C. by processing unit 39. As this present Example entailed the distillation of a fuel mixture, for safety considerations, processing unit 39 was programmed to deactivate cartridge heater 62 if second thermocouple 74 reached a temperature reading for the interior of distillation chamber 38 exceeding 285° C. Once temperature stabilized between 180° C. and 190° C., distillation of the fuel mixture containing the corrosion inhibitor additive continued for approximately another 6 minutes. At approximately 6 minutes, cartridge heater 62 was turned off. The first air flow controller for the air bubbler coupled to distillation chamber 38 was oriented to stop air flow to the air bubbler. After distillation, approximately 3 ml of the now concentrated fuel mixture containing the corrosion inhibitor additive remained in lower chamber 50 of distillation chamber 38. An exact volume of the concentrated fuel mixture containing the corrosion inhibitor additive was measured.

From distillation system 12, the concentrated fuel mixture containing the corrosion inhibitor additive was sent to input 26 of filtration system 14. The concentrated fuel mixture containing the corrosion inhibitor additive was then moved from input 26 and into first reservoir 28. Processing unit 39 then directed sample 1, approximately 1.2 ml of the concentrated fuel mixture containing the corrosion inhibitor additive, from first reservoir 28 into filter 32. Filter 32 was a tube approximately 18 to 24 inches in length and packed with a steel grit. The steel grit was chosen for this present Example as it targets and removes the corrosion inhibitor additive from the fuel mixture. The steel grit has a particle diameter averaging 300 microns and is composed of carbon, silicon, manganese and iron.

Sample 1 was sent through the steel grit of filter 32 into second reservoir 34. Once sample 1 exited filter 32, the air flow was stopped as air pump 22 was turned off by processing unit 39. Action from peristaltic pump 11 sent sample 1 from second reservoir 34 to third switch valve 20c then to fourth switch valve 20d and then to cuvette 80 of detector system 16.

Figure 8:
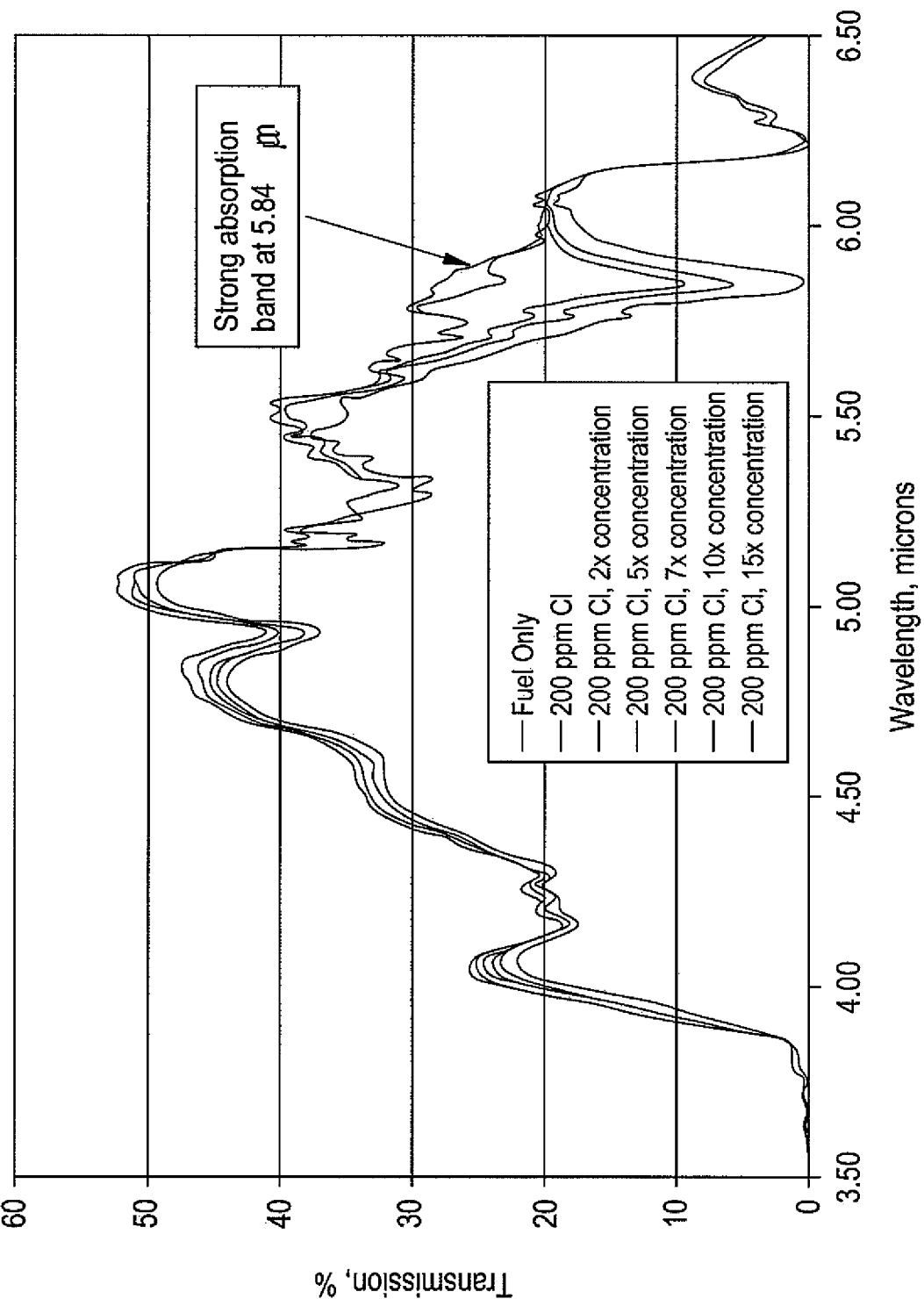
FIG. 8 is a graph depicting the primary wavelength for detection of a corrosion inhibitor additive in a fuel mixture.

For this present Example, we used a 10-position filter wheel in the detector system 16. For detection of the corrosion inhibitor additive in the concentrated fuel mixture, the primary wavelength was 5.84 μm as seen in FIG. 8 and was one position on the 10-position filter wheel. The remaining wavelengths on the 10-position filter wheel were chosen to characterize the signals from a plurality of chemicals or compounds in the concentrated fuel mixture that might interfere with the determination of the transmission spectra of the corrosion inhibitor additive at its primary wavelength. This characterization allowed for correction of possible interference by the plurality of chemicals or compounds in the concentrated fuel mixture at the primary wavelength of 5.84 μm.

Once sample 1 was deposited into cuvette 80, a first light beam transmitted by light source 82 moved through lens 84 and then through cuvette 80. The first light beam then moved to the spinning 10-position filter wheel and then to detector 83. The detector 83 determined the transmission spectra for sample 1.

Upon completion of the transmission spectra for sample 1, reference mirror 86 slid into position while the 10-position filter wheel stopped spinning. After approximately a half-second pause, the 10-position filter wheel began spinning again. A second light beam from light source 82 was reflected by reference mirror 86 to constant temperature cold plate 88, thus bypassing cuvette 80. From constant temperature cold plate 88, the second light beam focused on the 10-position filter wheel and was sent to detector 83, where detector 83 determined the transmission spectra for the background. Detector 83 sent the transmission spectra for sample 1 and the transmission spectra for the background to processing unit 39. Processing unit 39 computed a corrected transmission spectra for sample 1 correcting for the background. Sample 1 was moved from cuvette 80 to waste receptacle 13.

After sample 1 was deposited in waste receptacle 13, processing unit 39 directed sample 2, approximately 0.8 ml of the concentrated fuel mixture, from first reservoir 28 directly to third switch valve 20c, bypassing filter 32. Sample 2 then moved from third switch valve 20c to fourth switch valve 20d and then was deposited into cuvette 80. Once sample 2 was deposited in cuvette 80, the transmission spectra for sample 2 and for the background was determined in the same manner as above for sample 1. A corrected transmission spectra for sample 2 correcting for the background was then computed.

A corrected transmission spectra ratio for sample 1 to sample 2 was computed and stored by processing unit 39. The corrected transmission spectra ratio for sample 1 to sample 2 was then compared to a plurality of corrected transmission spectra ratios for a plurality of reference mixtures containing a range of known concentrations of the corrosion inhibitor additive. In this present Example, partial least squares regression was used to determine the concentration of the corrosion inhibitor additive in the fuel mixture by relating the corrected transmission spectra ratio for sample 1 to sample 2 to the plurality of corrected transmission spectra ratios for a plurality of reference samples containing a range of known concentrations of the corrosion inhibitor additive.

As will be understood by those familiar with the art, the present invention may be embodied in other specific forms without departing from the spirit or essential characteristics thereof. Accordingly, the disclosures and descriptions herein are intended to be illustrative, but not limiting, of the scope of the invention which is set forth in the following claims.

What is claimed is:

1. A method for determining the concentration of a substance in a mixture comprising a plurality of hydrocarbons, wherein the substance is a corrosion inhibitor, the method comprising:
   (a) directing a portion of the mixture to a substance removal device containing a steel substrate to create a first sample of the mixture;
   (b) providing a second sample from which the substance has not been removed;
   (c) measuring an absorption or transmission spectrum of the first sample and the second sample;
   (d) computing an absorption or transmission spectrum for the first sample relative to the second sample; and
   (e) determining the concentration of the substance in the mixture based on said absorption or transmission spectrum for the first sample relative to the second sample.

2. The method according to claim 1 wherein the steps of removing the substance from a portion of the mixture and measuring the absorption or transmission spectrum of the first sample and the mixture are carried out by an instrument that integrates a substance removal device, a transmission spectrometer and a fluid transport system that fluidly connects the substance removal device to a location arranged within the instrument to receive light transmitted by the transmission spectrometer.

3. The method according to claim 1 further comprising (f) increasing the concentration of the substance in the mixture prior to creating the first sample and prior to measuring the absorption or transmission spectrum of the mixture.

4. The method according to claim 3 wherein steps (f), (a), and (c) are carried out by an instrument that integrates a substance concentration device, a substance removal device, a spectrometer and a fluid transport system.

5. The method according to claim 1 further comprising raising the temperature of the mixture to increase the concentration of the substance in the mixture.

6. The method according to claim 1, in which the substance has a vapor pressure that is lower than that of the mixture, and comprising raising the temperature of the mixture to concentrate the substance prior to step (c).

7. The method of claim 1, in which the corrosion inhibitor has a lower vapor pressure than the hydrocarbon fuel, comprising concentrating the corrosion inhibitor in the mixture by raising the temperature of the mixture prior to steps (a) and (c), and in which the steel substrate is steel grit.

8. A method for analyzing a mixture containing a substance, wherein the mixture is a hydrocarbon fuel, and the substance is a corrosion inhibitor having a vapor pressure that is lower than that of the hydrocarbon fuel, the method comprising:
(a) directing a first sample of the mixture through a fluid transportation system to a substance removal device comprising a steel substrate that removes the substance from the first sample;
(b) directing the first sample from the substance removal device and through the fluid transportation system to a transmission spectrometer;
(c) directing a second sample of the mixture through the fluid transportation system to the transmission spectrometer;
(d) obtaining transmission spectra information for the first sample and the second sample; and
(e) calculating a value based upon the transmission spectra information for the first sample and the second sample.

9. The method according to claim 8 further comprising concentrating the substance in the mixture prior to removing the substance from the first sample and prior to directing the second sample through the fluid transportation system to the spectrometer.

10. The method according to claim 9 in which concentrating the substance is achieved by raising the temperature of the mixture in a distillation chamber prior to removing the substance from the first sample and prior to directing the second sample through the fluid transportation system to the spectrometer.

11. The method according to claim 10 wherein the distillation chamber, the substance removal device, the fluid transportation system, and the transmission spectrometer are contained within a selectively closeable carrying case.

12. The method according to claim 8 further comprising calculating the concentration of the substance in the mixture by comparing the value based upon the transmission spectra information for the first sample and the second sample to transmission spectra information of other mixtures containing known quantities of the substance.

13. The method according to claim 8 wherein the value based upon the transmission spectra information for the first sample and the second sample is a ratio of the transmission spectra information for the first sample and the second sample.

14. The method according to claim 8 wherein the value based upon the transmission spectra information for the first sample and the second sample is calculated as a difference between the transmission spectra information for the first sample and the second sample.

15. The method according to claim 8 wherein the value based upon the transmission spectra information for the first sample and the second sample is calculated as a weighted difference between the transmission spectra information for the first sample and the second sample.

16. The method according to claim 8 wherein the spectrum transmission value based upon the first sample and the second sample is calculated based upon the weighted difference between the spectrum transmission of the first sample and the second sample and the plurality of transmission spectrum values obtained from other mixtures containing known quantities of the substance is calculated based upon the weighted difference.

17. The method according to claim 8, in which the substance has a vapor pressure that is lower than that of the mixture, and comprising distilling the mixture to concentrate the substance prior to steps (b) and (c).

18. A method for analyzing a mixture that is a petroleum-based fuel containing a substance that is a corrosion inhibitor, the method comprising:
(a) preparing a first sample by removing the substance from a portion of the mixture by contacting the portion of the mixture with a steel substrate;
(b) measuring a first transmission spectrum of the first sample, wherein the first sample excludes the substance;
(c) measuring a second transmission spectrum of a second sample of the mixture, wherein the second sample includes the substance;
(d) calculating a spectrum transmission value based upon the first transmission spectrum and the second transmission spectrum; and
(e) comparing the spectrum transmission value to a plurality of transmission spectrum values obtained from other mixtures containing known quantities of the substance.

19. The method according to claim 18 wherein the other mixtures containing known quantities of the substance are prepared by obtaining a fraction of the mixture, removing essentially all of the substance from the fraction to form an substance-free mixture, separating the substance-free mixture into a plurality of samples, and adding varying, predetermined amounts of the substance to the plurality of samples.

20. The method according to claim 18 wherein the substance is removed by passing the portion of the mixture through a filter packed with steel grit.

21. The method according to claim 18 further comprising increasing the concentration of the substance in the mixture prior to measuring the second transmission spectrum of the second sample.

22. The method according to claim 18 wherein the steps of removing the substance from the mixture, measuring the first transmission spectrum of the first sample, and measuring the second transmission spectrum of the second sample of the mixture are performed by an instrument that integrates an substance removal device and a transmission spectrometer.

23. The method according to claim 22 wherein the instrument includes a substance concentration device for increasing the concentration of the substance in the mixture.

24. The method according to claim 18 wherein the steel substrate is steel grit.

25. The method according to claim 18 wherein the spectrum transmission value based upon the first sample and the second sample is a ratio of the spectrum transmission of the first sample and the second sample and the plurality of transmission spectrum values obtained from other mixtures containing known quantities of the substance is a ratio.

26. The method according to claim 18 wherein the spectrum transmission value based upon the first sample and the second sample is calculated based upon the difference between the spectrum transmission of the first sample and the second sample and the plurality of transmission spectrum values obtained from other mixtures containing known quantities of the substance is calculated based upon the difference.

27. The method according to claim 18, in which the substance has a vapor pressure that is lower than that of the mixture, and comprising distilling the mixture to concentrate the substance prior to steps (b) and (c).

* * * * *